US008929983B2

(12) United States Patent
Arcot-Krishnamurthy et al.

(10) Patent No.: US 8,929,983 B2
(45) Date of Patent: Jan. 6, 2015

(54) REVERSE HYSTERESIS AND MODE SWITCHING FOR INTERMITTENT PACING THERAPY

(75) Inventors: Shantha Arcot-Krishnamurthy, Vadnais Heights, MN (US); Gary T. Seim, Minneapolis, MN (US); Kent Lee, Shoreview, MN (US); Yanting Dong, Shoreview, MN (US); Allan C. Shuros, St. Paul, MN (US); David L. Whitehouse, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 564 days.

(21) Appl. No.: 12/615,050

(22) Filed: Nov. 9, 2009

(65) Prior Publication Data
US 2010/0121402 A1    May 13, 2010

Related U.S. Application Data

(60) Provisional application No. 61/113,073, filed on Nov. 10, 2008.

(51) Int. Cl.
*A61N 1/368*   (2006.01)
*A61N 1/362*   (2006.01)

(52) U.S. Cl.
CPC .............. *A61N 1/3627* (2013.01); *A61N 1/3688* (2013.01)
USPC ........ 607/25; 607/9; 607/11; 607/14; 607/16; 607/17; 607/18; 607/27; 607/115; 607/119; 607/123

(58) Field of Classification Search
CPC . A61N 1/3627; A61N 1/3684; A61N 1/3688; A61N 1/368; A61N 1/3702; A61N 1/365; A61N 1/36585; A61N 1/3624; A61N 1/362; A61N 1/37; A61N 1/36135; A61N 1/025; A61N 1/36128; A61B 5/04288; A61B 5/0452
USPC ......... 607/1–2, 9, 11, 14, 16–18, 25, 27, 115, 607/119, 123
See application file for complete search history.

(56) References Cited

U.S. PATENT DOCUMENTS

| 5,284,491 A | 2/1994 | Sutton et al. |
| 6,058,328 A | 5/2000 | Levine et al. |

(Continued)

FOREIGN PATENT DOCUMENTS

| WO | WO-93/02745 A1 | 2/1993 |
| WO | WO-99/10042 A1 | 3/1999 |

(Continued)

OTHER PUBLICATIONS

"U.S. Appl. No. 11/687,957, Notice of Allowance mailed Dec. 21, 2009", 8 pgs.

(Continued)

*Primary Examiner* — Deborah Malamud
(74) *Attorney, Agent, or Firm* — Schwegman Lundberg & Woessner, P.A.

(57) ABSTRACT

Cardioprotective pre-excitation pacing may be applied to stress or de-stress a particular myocardial region delivering of pacing pulses in a manner that causes a dyssynchronous contraction. Such dyssynchronous contractions are responsible for the desired cardioprotective effects of pre-excitation pacing. A method and device for applying reverse hysteresis and mode switching to the delivery of such cardioprotective pacing are described.

18 Claims, 5 Drawing Sheets

(56) References Cited

U.S. PATENT DOCUMENTS

| | | | |
|---|---|---|---|
| 7,295,874 B2* | 11/2007 | Prinzen et al. | 607/17 |
| 7,450,988 B2 | 11/2008 | Ross et al. | |
| 2003/0130702 A1 | 7/2003 | Kramer et al. | |
| 2005/0065568 A1 | 3/2005 | Liu et al. | |
| 2006/0149326 A1* | 7/2006 | Prinzen et al. | 607/17 |
| 2006/0241704 A1 | 10/2006 | Shuros et al. | |
| 2006/0247702 A1 | 11/2006 | Stegemann et al. | |
| 2006/0259087 A1 | 11/2006 | Baynham et al. | |
| 2006/0259088 A1 | 11/2006 | Pastore et al. | |
| 2006/0287684 A1 | 12/2006 | Baynham et al. | |
| 2007/0150005 A1 | 6/2007 | Sih et al. | |
| 2007/0191892 A1 | 8/2007 | Mullen et al. | |
| 2008/0004669 A1 | 1/2008 | Sathaye et al. | |
| 2008/0221636 A1 | 9/2008 | Pastore et al. | |
| 2008/0234774 A1 | 9/2008 | Baynham et al. | |

FOREIGN PATENT DOCUMENTS

| | | | |
|---|---|---|---|
| WO | WO-2004/024229 A1 | 3/2004 | |
| WO | WO-2006/105474 A2 | 10/2006 | |
| WO | WO-2010/054359 A2 | 5/2010 | |

OTHER PUBLICATIONS

"U.S. Appl. No. 11/687,957, Non-Final Office Action mailed Mar. 6, 2009", 7 pgs.

"U.S. Appl. No. 11/687,957, Response filed Aug. 6, 2009 to Non-Final Office Action mailed Mar. 6, 2009", 17 pgs.

"International Application No. PCT/US2008/003594, Written Opinion mailed Jul. 9, 2008", 6 pgs.

"International Application No. PCT/US2008/003594, Interrnational Search Report mailed Jul. 9, 2008", 5 pgs.

"International Application Serial No. PCT/US2009/063830, Invitation to Pay Additional Fees and Partial International Search mailed Mar. 19, 2010", 6 pgs.

Ciampi, Q., et al., "Identification of responders to cardiac resynchronication therapy by contractile reserve during stress echocardiography", *European Journal of Heart Failure 11*, (Mar. 26, 2009), 489-496.

Lancellotti, Patrizio, et al., "Myocardial contractile reserve during exercise predicts left ventricular reverse modelling after cardiac resynchronication therapy", *European Journal of Echocardiography*, (Apr. 7, 2009), 6 pgs.

Lim, Pascal, et al., "Importance of contractile reserve for CRT", *Europace 9*, (Jun. 2007), 739-743.

Naqvi, Tasneem Z., et al., "Myocardial Contractile Reserve on Dobutamine Echocardiography Predicts Late Spontaneous Improvement in Cardiac Function in Patients with Recent Onset Idiopathic Dilated Cardiomyopathy", *Journal of the American College of Cardiology 34*(5), (Nov. 1, 1999), 1537-1544.

Ohshima, Satoru, et al., "Cardiac Sympathetic Dysfunction Correlates with Abnormal Myocardial Contractile Reserve in Dilated Cardiomyopathy Patients", *Journal of the American College of Cardiology 46*(11), (Dec. 6, 2005), 2061-2068.

Otasevic, Petar, et al., "Right vs. left ventricular contractile reserve in one-year prognosis of patients with idiopathic dilated cardiomyopathy: Assessment by dobutamine stress echcardiography", *Eur J Echocardiography 6*, (Mar. 31, 2005), 429-434.

Ovize, M., et al., "Stretch preconditions canine myocardium.", *Am J Physiol.*, 266(1 Pt 2), (Jan. 1994), H137-H146.

Prinzen, F. W., et al., "Relation between the pacing induced sequence of activation and left ventricular pump function in animals.", *Pacing Clin Electrophysiol.*, 25(4 Pt 1), (Apr. 2002), 484-498.

Prinzen, F. W., "Mapping of regional myocardial strain and work during ventricular pacing: experimental study using magnetic resonance imaging tagging", *Journal of the American College of Cardiology*, 33(6), (May 1999), 1735-1742.

Scrutinio, D., et al., "Low-dose dobutamine responsiveness in idiopathic dilated cardiomyopathy: relation to exercise capacity and clinical outcome", *European Heart Journal 21*(11), (Jun. 2000), 927-934.

Vanagt, W. Y., et al., "Pacing-induced dys-synchrony preconditions rabbit myocardium against ischemia/reperfusion injury.", *Circulation*, 114(1 Supply, (Jul. 4, 2006), 1264-1269.

"International Application Serial No. PCT/US2009/063830, International Search Report mailed Aug. 20, 2010", 6 pgs.

"International Application Serial No. PCT/US2009/063830, Written Opinion mailed Aug. 20, 2010", 8 pgs.

* cited by examiner

REVERSE HYSTERESIS AND MODE SWITCHING FOR INTERMITTENT PACING THERAPY

RELATED APPLICATIONS

This application claims the benefit of U.S. Provisional Application No. 61/113,073, filed on Nov. 10, 2008, under 35 U.S.C. §119(e), which is hereby incorporated by reference in its entirety.

This application is related to U.S. patent application Ser. No. 11/687,957 filed on Mar. 19, 2007, now issued as U.S. Pat. No. 7,711,420, and assigned to Cardiac Pacemakers, Inc., the disclosure of which is incorporated by reference in its entirety.

FIELD OF THE INVENTION

This invention pertains to cardiac rhythm management devices such as pacemakers and other implantable devices.

BACKGROUND

Heart failure (HF) is a debilitating disease that refers to a clinical syndrome in which an abnormality of cardiac function causes a below normal cardiac output that can fall below a level adequate to meet the metabolic demand of peripheral tissues. Heart failure can be due to a variety of etiologies with ischemic heart disease being the most common. Inadequate pumping of blood into the arterial system by the heart is sometimes referred to as "forward failure," with "backward failure" referring to the resulting elevated pressures in the lungs and systemic veins which lead to congestion. Backward failure is the natural consequence of forward failure as blood in the pulmonary and venous systems fails to be pumped out. Forward failure can be caused by impaired contractility of the ventricles due, for example, to coronary artery disease, or by an increased afterload (i.e., the forces resisting ejection of blood) due to, for example, systemic hypertension or valvular dysfunction. One physiological compensatory mechanism that acts to increase cardiac output is due to backward failure which increases the diastolic filling pressure of the ventricles and thereby increases the preload (i.e., the degree to which the ventricles are stretched by the volume of blood in the ventricles at the end of diastole). An increase in preload causes an increase in stroke volume during systole, a phenomena known as the Frank-Starling principle. Thus, heart failure can be at least partially compensated by this mechanism but at the expense of possible pulmonary and/or systemic congestion.

When the ventricles are stretched due to the increased preload over a period of time, the ventricles become dilated. The enlargement of the ventricular volume causes increased ventricular wall stress at a given systolic pressure. Along with the increased pressure-volume work done by the ventricle, this acts as a stimulus for hypertrophy of the ventricular myocardium which leads to alterations in cellular structure, a process referred to as ventricular remodeling. Ventricular remodeling leads to further dysfunction by decreasing the compliance of the ventricles (thereby increasing diastolic filling pressure to result in even more congestion) and causing eventual wall thinning that causes further deterioration in cardiac function. It has been shown that the extent of ventricular remodeling is positively correlated with increased mortality in HF patients.

Remodeling is thought to be the result of a complex interplay of hemodynamic, neural, and hormonal factors that occur primarily in response to myocardial wall stress. As noted above, one physiological compensatory mechanism that acts to increase cardiac output is increased diastolic filling pressure of the ventricles as an increased volume of blood is left in the lungs and venous system, thus increasing preload. The ventricular dilation resulting from the increased preload causes increased ventricular wall stress at a given systolic pressure in accordance with Laplace's law. Along with the increased pressure-volume work done by the ventricle, this acts as a stimulus for compensatory hypertrophy of the ventricular myocardium. Hypertrophy can increase systolic pressures but, if the hypertrophy is not sufficient to meet the increased wall stress, further and progressive dilation results. This non-compensatory dilation causes wall thinning and further impairment in left ventricular function. It also has been shown that the sustained stresses causing hypertrophy may induce apoptosis (i.e., programmed cell death) of cardiac muscle cells. Although ventricular dilation and hypertrophy at first may be compensatory and increase cardiac output, the process ultimately results in further deterioration and dysfunction.

DETAILED DESCRIPTION

Described herein is a method and device for delivering electrical stimulation to the heart in a manner that advantageously redistributes myocardial stress during systole for therapeutic purposes in the treatment of, for example, patients with ischemic heart disease, post-MI patients, and HF patients. Myocardial regions that contract earlier during systole experience less wall stress than later contracting regions. Pacing pulses may be delivered to a particular myocardial region to pre-excite that region relative to other regions during systole, with the latter being excited by intrinsic activation or a subsequent pacing pulse. (As the term is used herein, a pacing pulse is any type of electrical stimulation that excites the myocardium, whether or not used to enforce a particular rate.) As compared with an intrinsic contraction, the pre-excited region is mechanically unloaded or de-stressed, while the later excited regions are subjected to increased stress. Such pre-excitation pacing may be applied to deliberately de-stress a particular myocardial region that may be expected to undergo deleterious remodeling, such as the area around a myocardial infarct or a hypertrophying region. Pre-excitation pacing may also be applied to deliberately stress a region remote from the pre-excitation pacing site in order to exert a conditioning effect, similar to the beneficial effects of exercise. Whether for intentionally stressing or de-stressing a myocardial region, such cardioprotective pre-excitation pacing may be applied intermittently, either according to a defined schedule or upon detection of specified entry or exit conditions, and is referred to herein as intermittent pacing therapy or IPT.

As explained above, pacing pulses may be used to pre-excite a region of the heart so that it contracts before later-excited regions and experiences less stress during systole.

This is in contradistinction to the normal physiological situation where, due the heart's specialized conduction system, the spread of depolarization throughout the myocardium is very rapid and results in a synchronous contraction. If the contractility of the myocardial tissue is normal, a synchronous contraction is hemodynamically more effective in pumping blood. Cardiac resynchronization pacing attempts to restore synchronous contractions in patients having ventricular conduction abnormalities by delivering pacing pulses to the heart in a manner that results in a more synchronous contraction than would otherwise occur. Pre-excitation pacing applied to stress or de-stress a particular myocardial region for a cardioprotective effect, on the other hand, is the delivery of pacing pulses in a manner that causes a dyssynchronous contraction. Such dyssynchronous contractions are responsible for the desired cardioprotective effects of pre-excitation pacing. Described herein is a method and device for delivering IPT in a manner that increases its effectiveness as the patient's intrinsic heart rate changes.

Mechanical Effects of Pacing Therapy

When the ventricles are stimulated to contract by a pacing pulse applied through an electrode located at a particular pacing site, the excitation spreads from the pacing site by conduction through the myocardium. This is different from the normal physiological situation, where the spread of excitation to the ventricles from the AV node makes use of the heart's specialized conduction system made up of Purkinje fibers which allows a rapid and synchronous excitation of the entire ventricular myocardium. The excitation resulting from a pacing pulse, on the other hand, produces a relatively asynchronous contraction due to the slower velocity at which excitation is conducted from the pacing site to the rest of the myocardium. Regions of the myocardium located more distally from the pacing site are thus excited later than regions proximal to the pacing site as compared with an intrinsic contraction. As explained below, this results in a re-distribution of myocardial wall stress.

The degree of tension on a muscle fiber before it contracts is termed the preload, while the degree of tension on a muscle fiber as it contracts is termed the afterload. Increasing the preload stretches a muscle fiber and also increases its maximum tension and velocity of shortening during contraction. With respect to the heart, the preload of a particular myocardial region is the myocardial wall stress at the end of diastole due to end-diastolic pressure and the forces applied by adjacent regions. The afterload of a myocardial region is the myocardial wall stress during systole due to the pressure load that the heart must pump against. When a myocardial region contracts late relative to other regions, the contraction of those other regions stretches the later contracting region and increases its preloading, thus causing an increase in the contractile force generated by the region. Conversely, a myocardial region that contracts earlier relative to other regions experiences decreased preloading and generates less contractile force. Because pressure within the ventricles rises rapidly from a diastolic to a systolic value as blood is pumped out into the aorta and pulmonary arteries, the parts of the ventricles that contract earlier during systole do so against a lower afterload than do parts of the ventricles contracting later. Delivery of a pacing pulse to a ventricular region makes that region contract earlier than other parts of the ventricle. The paced region will therefore be subjected to both a decreased preload and afterload which decreases the mechanical stress experienced by the region relative to other regions during systolic contraction. A region remote from the paced region, on the other hand, will experience increased mechanical stress as it contracts later during systole due to either conduction from the pre-excited site, a subsequent pace applied to the remote region, or intrinsic activation conducted from the AV node.

Applications of Stress Reducing Pre-Excitation Pacing

All but a small fraction of the total amount of oxygen consumed by the myocardium is for the purpose of active muscular contraction during systole, and the oxygen demand of a particular myocardial region increases with increasing systolic wall stress. Causing a particular myocardial region to contract earlier relative to other regions will thus lessen its metabolic demands and the degree of any ischemia that may be present. Particular myocardial regions may also be vulnerable to undergoing deleterious remodeling as a result of increased wall stress in post-MI or HF patients. In order to cause early contraction and lessened stress to a myocardial region vulnerable to becoming ischemic or undergoing remodeling, pre-excitation pacing pulses may be delivered to one or more sites in or around the vulnerable region in a manner that pre-excites those sites relative to the rest of the ventricle and mechanically unloads the vulnerable region. Pre-excitation pacing therapy to unload a vulnerable region may be implemented by pacing the ventricles at a single site in proximity to the vulnerable region or by pacing at multiple ventricular sites in such proximity. In the latter case, the pacing pulses may be delivered to the multiple sites simultaneously or in a defined pulse output sequence. The single-site or multiple site pacing may be performed in accordance with a bradycardia pacing algorithm such as an inhibited demand mode or a triggered mode.

Applications of Stress Augmenting Pre-Excitation Pacing

Another use of pre-excitation pacing is to intentionally stress a region vulnerable to ischemia by pacing at a site(s) remote from the vulnerable region. As described above, such pacing causes increased mechanical stress to the vulnerable region by delaying its contraction during systole relative to other regions. Intermittently stressing a vulnerable region may cause a low level of myocardial ischemia in the region in a patient with demand ischemia, thereby promoting angiogenesis and pre-conditioning the vulnerable region to better withstand the effects of a subsequent ischemic episode. Stress augmentation pacing may also be applied to a weakened region or to a large part of the myocardium in the form of an asynchronous contraction in order to exert a pre-conditioning effect similar to exercise. Pre-excitation pacing therapy to augment stress may be implemented by pacing the ventricles at a single site or multiple sites remote from the region(s) desired to be stressed in accordance with a bradycardia pacing algorithm such as an inhibited demand mode or a triggered mode. Multiple pacing pulses may be delivered to the multiple sites simultaneously or in a defined pulse output sequence.

Exemplary Implantable Device

Figure 1:
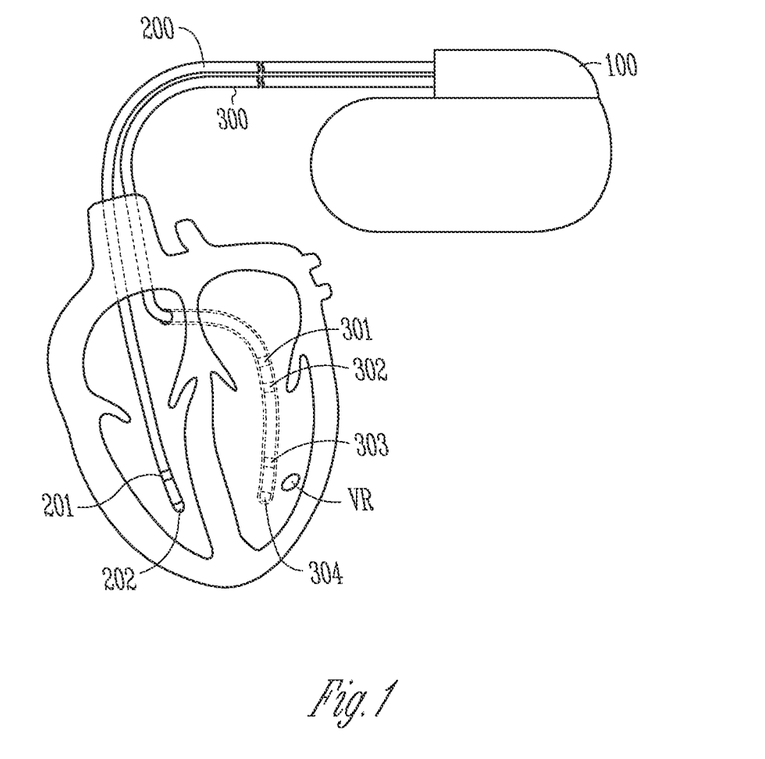
FIG. 1 illustrates the physical configuration of an exemplary pacing device.

FIG. 1 shows an exemplary implantable cardiac device 100 for delivering pre-excitation pacing for the purpose of stressing or de-stressing one or more myocardial regions. In addition, the device may have the capability of delivering other types of pacing therapy such as bradycardia pacing and cardiac resynchronization pacing. As will be described below, the device may be configured to switch between a normal operating mode and a pre-excitation mode for delivering pre-excitation pacing in accordance with defined entry and exit conditions. Implantable pacing devices are typically placed subcutaneously or submuscularly in a patient's chest with leads threaded intravenously into the heart to connect the device to electrodes disposed within a heart chamber that are used for sensing and/or pacing of the chamber. Electrodes may also be positioned on the epicardium by various means.

A programmable electronic controller causes the pacing pulses to be output in response to lapsed time intervals and/or sensed electrical activity (i.e., intrinsic heart beats not as a result of a pacing pulse). The device senses intrinsic cardiac electrical activity through one or more sensing channels, each of which incorporates one or more of the electrodes. In order to excite myocardial tissue in the absence of an intrinsic beat, pacing pulses with energy above a certain threshold are delivered to one or more pacing sites through one or more pacing channels, each of which incorporates one or more of the electrodes. FIG. 1 shows the exemplary device having two leads 200 and 300, each of which is a multi-polar (i.e., multi-electrode) lead having electrodes 201-202 and 301-304, respectively. The electrodes 201-202 are disposed in the right ventricle in order to excite or sense right ventricular and/or septal regions, while the electrodes 301-304 are disposed in the coronary sinus or left cardiac veins in order to excite or sense regions of the left ventricle. If a region VR that is vulnerable to remodeling or ischemia were located in the apical region of the left ventricle, pre-excitation pacing to the region could be delivered via electrodes 303 and 304 in a bipolar pacing configuration to de-stress and unload the vulnerable region. Such pre-excitation pacing could be delivered, for example, as left ventricular-only pacing or as biventricular pacing with an offset such that the left ventricle is paced before the right. Conversely, if it were desired to deliberately stress the region VR for cardioprotective pre-conditioning, pre-excitation pacing could be delivered via electrodes 201 and 202 in a right ventricle-only pacing mode or electrodes 301 and 302 in a left ventricle-only or biventricular pacing mode in order to pre-excite a myocardial region remote from the region VR. Other embodiments may use any number of electrodes in the form of unipolar and/or multi-polar leads in order to excite different myocardial sites. As explained below, once the device and leads are implanted, the pacing and/or sensing channels of the device may be configured with selected ones of the multiple electrodes in order to selectively pace or sense a particular myocardial site(s).

Figure 2:
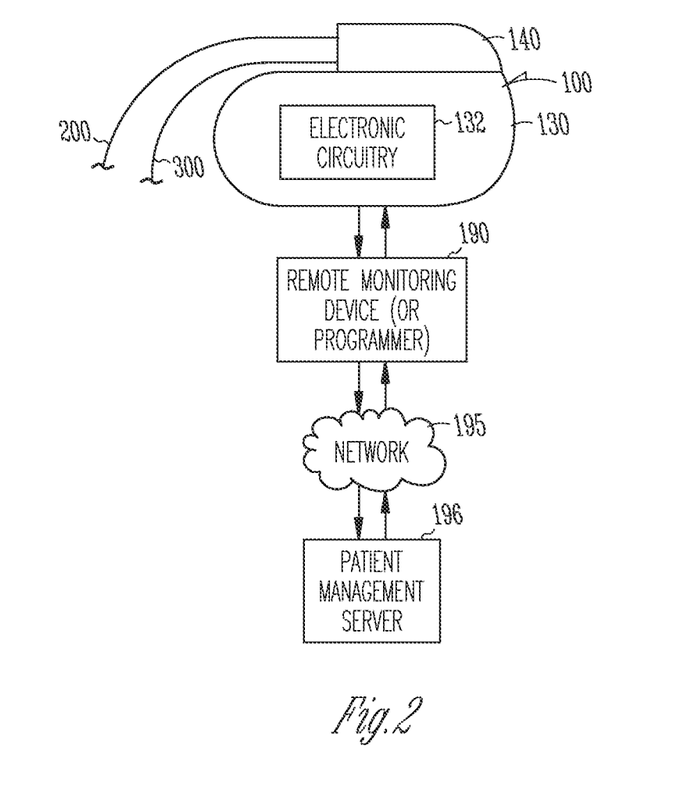
FIG. 2 shows the components of an exemplary device.

FIG. 2 shows the components of the implantable device 100 in more detail as well as an exemplary monitoring/programming system. The implantable device 100 includes a hermetically sealed housing 130 that is placed subcutaneously or submuscularly in a patient's chest. The housing 130 may be formed from a conductive metal, such as titanium, and may serve as an electrode for delivering electrical stimulation or sensing in a unipolar configuration. A header 140, which may be formed of an insulating material, is mounted on the housing 130 for receiving leads 200 and 300 which may be then electrically connected to pulse generation circuitry and/or sensing circuitry. Contained within the housing 130 is the electronic circuitry 132 for providing the functionality to the device as described herein which may include a power supply, sensing circuitry, pulse generation circuitry, a programmable electronic controller for controlling the operation of the device, and a telemetry transceiver capable of communicating with an external programmer or a remote monitoring device 190. An external programmer wirelessly communicates with the device 100 and enables a clinician to receive data and modify the programming of the controller. A remote monitoring device also communicates via telemetry with the device 100 and may be further interfaced to a network 195 (e.g., an internet connection) for communicating with a patient management server 196 that allows clinical personnel at remote locations to receive data from the remote monitoring device as well as issue commands. The controller may be programmed such when particular conditions are detected by the monitoring circuitry (such as when a measured parameter exceeds or falls below a specified limit value), the device transmits an alarm message to the remote monitoring device and to the patient management server to alert clinical personnel. The mode used for delivery of IPT can be trended, which trending can be made available for viewing on a programmer or a patient management system. Such trending can also be applied to parameter changes relating to reverse hysteresis as described below. More specifically, the modes used for IPT delivery, the number of times that IPT was aborted, the mean/median LRL used, and the mean/median AV delay used can be trended.

Figure 3:
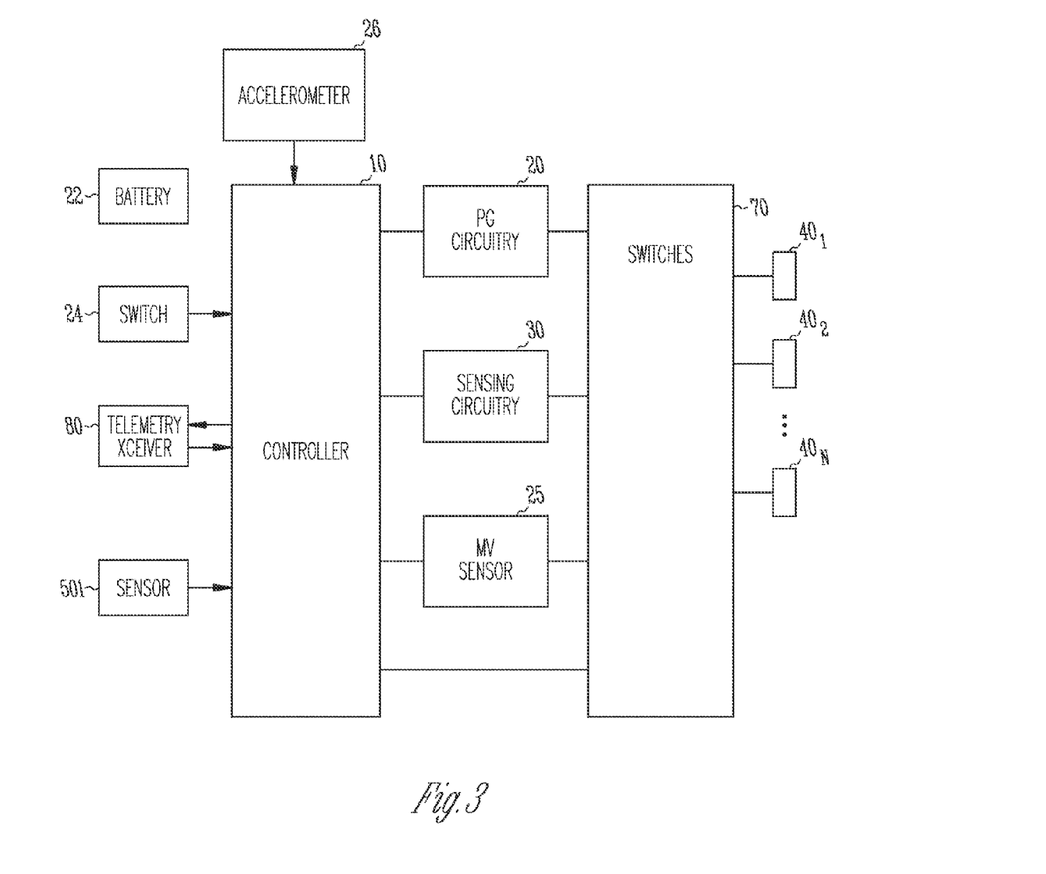
FIG. 3 is a block diagram of the electronic circuitry of an exemplary device.

A block diagram of the circuitry 132 is illustrated in FIG. 3. A battery 22 supplies power to the circuitry. The controller 10 controls the overall operation of the device in accordance with programmed instructions and/or circuit configurations. The controller may be implemented as a microprocessor-based controller and include a microprocessor and memory for data and program storage, implemented with dedicated hardware components such as ASICs (e.g., finite state machines), or implemented as a combination thereof. The controller also includes timing circuitry such as external clocks for implementing timers used to measure lapsed intervals and schedule events. As the term is used herein, the programming of the controller refers to either code executed by a microprocessor or to specific configurations of hardware components for performing particular functions. A telemetry transceiver 80 is interfaced to the controller which enables the controller to communicate with an external programmer and/or a remote monitoring unit. A magnetically or tactilely actuated switch 24 is also shown as interfaced to the controller to allow the patient to signal certain conditions or events to the implantable device. Sensing circuitry 30 and pulse generation circuitry 20 are interfaced to the controller by which the controller interprets sensing signals and controls the delivery of pacing pulses in accordance with a pacing mode. The sensing circuitry 30 receives atrial and/or ventricular electrogram signals from sensing electrodes and includes sensing amplifiers, analog-to-digital converters for digitizing sensing signal inputs from the sensing amplifiers, and registers that can be written to for adjusting the gain and threshold values of the sensing amplifiers. The pulse generation circuitry 20 delivers pacing pulses to pacing electrodes disposed in the heart and includes capacitive discharge pulse generators, registers for controlling the pulse generators, and registers for adjusting pacing parameters such as pulse energy (e.g., pulse amplitude and width). The device allows adjustment of the pacing pulse energy in order to ensure capture of myocardial tissue (i.e., initiating of a propagating action potential) by a pacing pulse. The pulse generation circuitry may also include a shocking pulse generator for delivering a defibrillation/cardioversion shock via a shock electrode upon detection of a tachyarrhythmia.

A pacing channel is made up of a pulse generator connected to an electrode, while a sensing channel is made up of a sense amplifier connected to an electrode. Shown in the figure are electrodes $40_1$ through $40_N$ where N is some integer. The electrodes may be on the same or different leads and are electrically connected to a MOS switch matrix 70. The switch matrix 70 is controlled by the controller and is used to switch selected electrodes to the input of a sense amplifier or to the output of a pulse generator in order to configure a sensing or pacing channel, respectively. The device may be equipped with any number of pulse generators, amplifiers, and electrodes that may be combined arbitrarily to form sensing or pacing channels. The switch matrix 70 allows selected ones of the available implanted electrodes to be incorporated into sensing and/or pacing channels in either unipolar or bipolar configurations. A bipolar sensing or pacing configuration refers to the sensing of a potential or output of a pacing pulse between two closely spaced electrodes, where the two electrodes are usually on the same lead (e.g., a ring and tip electrode of a bipolar lead or two selected electrodes of a multi-polar lead). A unipolar sensing or pacing configuration is where the potential sensed or the pacing pulse output by an electrode is referenced to the conductive device housing or another distant electrode.

The device illustrated in FIG. 3 may be configured with multiple sensing and/or pacing channels that may be either atrial or ventricular channels depending upon the location of the electrode. The device is therefore capable of delivering single-site or multiple site ventricular pre-excitation pacing for purposes of stress reduction/augmentation as well as conventional pacing. The switch matrix allows particular myocardial sites to be pre-excited for purposes of stress reduction or augmentation by selecting the appropriately disposed electrode(s) to be incorporated into a pacing channel used to deliver pre-excitation pacing. Configuration of pacing and sensing channels may be performed via an external programmer communicating through the telemetry interface as well as automatically by the device when switching to or from different pacing modes.

Pre-excitation pacing may be delivered as single-site pacing, biventricular pacing where one of the ventricles is pre-excited relative to the other as determined by a programmed biventricular offset interval, or delivered as multi-site ventricular pacing. In the case where the pre-excitation pacing is delivered at multiple sites, the sites may be paced simultaneously or in accordance with a particular pulse output sequence that specifies the order and timing in which the sites are to be paced during a single beat. When an electrogram signal in an atrial or ventricular sensing channel exceeds a specified threshold, the controller detects an atrial or ventricular sense, respectively, which pacing algorithms may employ to trigger or inhibit pacing. The controller is capable of operating the device in a number of programmed modes where a programmed mode defines how pacing pulses are output in response to sensed events and expiration of time intervals. Pre-excitation pacing of one or more ventricular sites in proximity to, or remote from, a vulnerable region may be delivered in conjunction with a bradycardia pacing mode, which refers to a pacing algorithm that enforces a certain minimum heart rate, and may include or not include pacing pulses delivered to the atria or ventricles for other purposes (e.g., treatment of bradycardia). Inhibited demand bradycardia pacing modes utilize escape intervals to control pacing in accordance with sensed intrinsic activity. In an inhibited demand ventricular pacing mode, the ventricle is paced during a cardiac cycle only after expiration of a defined escape interval during which no intrinsic beat by the chamber is detected. For example, a ventricular escape interval can be defined between ventricular events so as to be restarted with each ventricular sense or pace, referred to as a lower rate interval (LRI). The inverse of this escape interval is the minimum rate at which the pacemaker will allow the ventricles to beat, sometimes referred to as the lower rate limit (LRL). Paces may also be delivered in a rate-adaptive pacing mode where the escape intervals are modified in accordance with a measured exertion level such as with accelerometer 26 or minute ventilation sensor 25. In atrial tracking and AV sequential pacing modes, another ventricular escape interval is defined between atrial and ventricular events, referred to as the atrio-ventricular delay or AVD interval. The atrio-ventricular delay interval is triggered by an atrial sense or pace and stopped by a ventricular sense or pace. A ventricular pace is delivered upon expiration of the atrio-ventricular delay interval if no ventricular sense occurs before the expiration.

In one embodiment, a cardiac rhythm management device includes at least one pacing channel for delivering pacing pulses to a selected ventricular myocardial site and a controller for controlling the delivery of pacing pulses in accordance with a programmed pacing mode. The controller is programmed to intermittently switch from a normal operating mode to an IPT mode in which a particular region or regions of the ventricular myocardium are subjected to increased or decreased mechanical stress as compared with the stress experienced by those regions during the normal operating mode. The normal operating mode may be a mode in which no pacing therapy is delivered or may be a primary pacing mode for delivering ventricular and/or atrial pacing therapy where the IPT pacing mode causes a different depolarization pattern than the primary pacing mode by, for example, exciting the ventricular myocardium at a site or sites different from the primary pacing mode or with different timing relationships between senses or paces. The switch from a primary pacing mode to an IPT mode may involve switching from bipolar pacing to unipolar pacing or vice-versa, switching which electrode of a bipolar pacing lead is the cathode and which electrode is the anode, switching from left ventricle-only pacing to right ventricular pacing or vice-versa, switching from biventricular pacing to no pacing at all or vice-versa, switching from biventricular pacing to single ventricular pacing or vice-versa, using at least one pacing channel in the stress augmentation mode that not used in the primary pacing mode, switching between different bradycardia pacing modes (e.g., between VVI and an atrial tracking or AV sequential mode), or modifying one or more escape intervals such as the AVD or LRL (e.g., the IPT mode may involve higher rate pacing, overdrive pacing, or may involve pacing with a shortened AVD such as an AVD specified as a percentage of the patient's intrinsic atrio-ventricular interval). The controller may be programmed to deliver IPT intermittently according to specified duty cycles as scheduled by an internal timer. For example, the scheduled duty cycles may specify that IPT is to be turned on for five minutes and turned off for five minutes in a repetitive manner over a predetermined time period.

Intermittent Pacing Therapy with Reverse Hysteresis

Ventricular dyssynchrony is the desired result of pre-excitation pacing to redistribute myocardial stress for a cardioprotective effect. Such dyssynchrony is what is responsible for causing the difference in stress experienced by the pre-excited and later-excited regions. As discussed above, intermittent periods of cardiac stress brought about by pacing therapy that produces relatively asynchronous cardiac contractions can exert a cardioprotective effect that reverses deleterious cardiac remodeling and/or provides protection against subsequent ischemic episodes. Described herein is a method and device for delivering intermittent pacing therapy (IPT) in a manner dependent upon a patient's heart rate that increases the effectiveness of IPT.

A pacemaker operating in a bradycardia demand mode may employ hysteresis in its control algorithm to vary the escape interval for the purpose of encouraging intrinsic beats. Hysteresis with respect to the lower rate limit means that if the heart starts to beat intrinsically at a rate above the lower rate limit, so that the pacemaker is not having to pace the heart, the lower rate limit is lowered to a hysteresis value. That is, the next pacing escape interval is prolonged to a hysteresis value after a spontaneous, or natural beat. The intrinsic heart rate must then fall below the hysteresis value before the pacemaker starts to pace the heart again, at which point the lower rate limit is returned to its original value. The advantage of hysteresis is that it enables the pacemaker to follow a natural rhythm that is just slightly below the original programmed lower rate limit (LRL) but still at a high enough rate that it is not necessary to override these natural beats with pacing. Hysteresis may also be applied with respect to the atrial escape interval to enable increased tracking of natural atrial beats. As described below, reverse hysteresis, where a pacing escape interval is varied in to order to promote paced beats rather than intrinsic ones, may be beneficially applied in the delivery of IPT.

Since it is the asynchronous cardiac contractions brought about by pacing during IPT that are responsible for its therapeutic effects, the effectiveness of IPT is diminished during those cardiac cycles when the patient's heart rate is high enough to inhibit pacing. It may thus be desirable to shorten one or more of the escape intervals used to deliver pacing in the IPT mode. For example, the ventricular escape interval (i.e., the escape interval between ventricular beats that is the inverse of the LRL), the atrial escape interval used to pace the atria, and/or the AV delay used in atrial tracking and AV sequential modes may be shortened in the IPT mode as compared with the normal mode. In certain situations, it may even be the case that the shortened escape interval(s) are all that distinguishes the IPT mode from the normal mode. In order to increase the probability of paced beats during IPT, a reverse hysteresis algorithm may be applied to adapt the escape interval(s) used to deliver pacing as the patient's intrinsic heart rate changes. Such reverse hysteresis may be applied to ventricular escape interval, the atrial escape interval, and/or the AV delay.

For example, IPT may involve pacing the ventricles in a non-atrial tracking ventricular pacing mode such as VVI in which a pace is delivered upon expiration of a ventricular escape interval started by a ventricular sense or pace. This escape interval, which is the inverse of the lower rate limit, may be shortened to some predetermined value for the IPT mode so that the LRL is above the patient's expected natural rate. The value of the LRL for the IPT mode may also be a function of a measured exertion level (i.e., be a sensor-indicated rate) or a measured intrinsic heart rate. In order to apply reverse hysteresis to the IPT mode in this example, the ventricular escape interval is further shortened by some amount (e.g., by a certain percentage or by a fixed number of milliseconds) if a ventricular sense (or specified number of ventricular senses) occurs during the IPT. The IPT is then delivered with the shortened ventricular escape interval for the duration of the IPT mode or the escape interval may be shortened during the IPT for only a fixed period of time or number of beats. Such shortening of the escape interval may be repeated each time a ventricular sense (or specified number of ventricular senses) occurs until a specified minimum limit value (i.e., a maximum LRL) is reached. At that point, the IPT mode may continue for its prescribed duration with the presently used LRL or may be discontinued until the next IPT mode switch. A similar algorithm may be applied for the atrial escape interval used to deliver atrial pacing in atrial pacing modes such as AAI or in atrial-ventricular pacing modes such as DDD.

In another example, reverse hysteresis is applied to the atrio-ventricular escape interval or AV delay when IPT is delivered as ventricular pacing using an atrial tracking pacing mode such as VDD or DDD. After switching to the IPT mode, the AV delay is set to some programmed value or to a value that is a function of a previously measured intrinsic atrio-ventricular interval. The value of the initial AV delay would normally be one that is expected to deliver ventricular paces during nearly all cardiac cycles. If a ventricular pace is inhibited by a ventricular sense (or if ventricular sense occurs during a specified number of cardiac cycles), the AV delay is shortened by some amount (e.g., by a fixed number of milliseconds or by a percentage of the present AV delay). The IPT is then delivered with the shortened AV delay for the duration of the IPT mode or the AV delay may be shortened during the IPT for only a fixed period of time or number of beats. Such shortening of the AV delay may be repeated each time a ventricular sense (or specified number of ventricular senses) occurs until a specified minimum limit value is reached. At that point, the IPT mode may continue for its prescribed duration with the presently used AV delay or may be discontinued until the next IPT mode switch.

Figure 4:
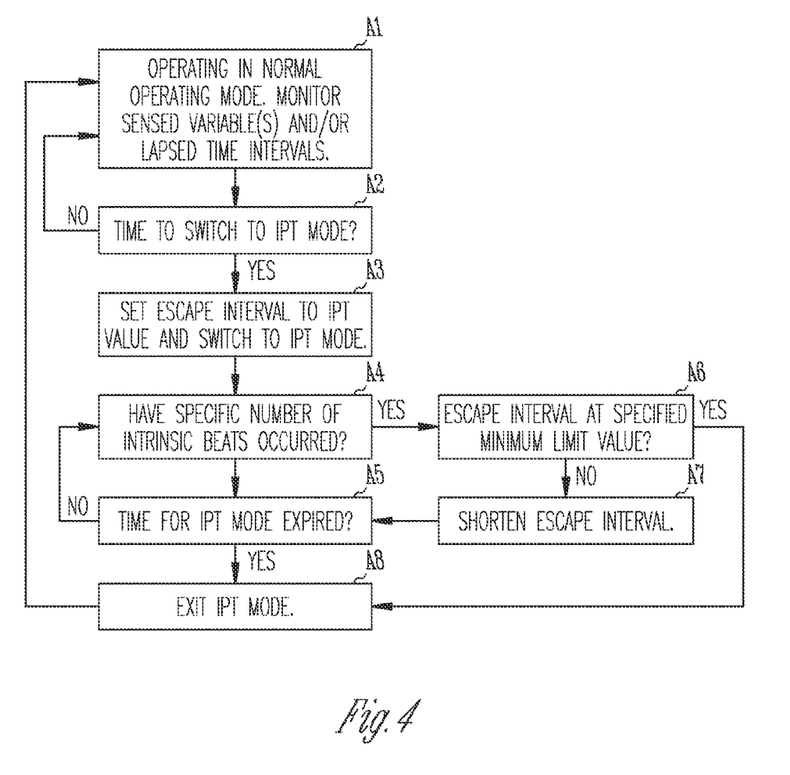
FIG. 4 illustrates an exemplary algorithm for implementing reverse hysteresis with respect to an IPT escape interval.

FIG. 4 illustrates an algorithm that could be executed by the device controller in order to apply reverse hysteresis to an escape interval during IPT. At state A1, the device operates in a normal operating mode while monitoring lapsed time intervals and/or one or more sensed variables and checks at state A2 if it is time to switch to the IPT mode. The scheduling of the IPT mode may be based upon timed intervals and/or upon one or more sensed conditions being present (e.g., when the patient's heart rate and/or measured exertion level is within a particular range. The duration of the IPT mode may also be based upon lapsed time intervals and/or sensed conditions. When it is determined that a switch to the IPT mode is to be made, the relevant escape interval (e.g., a ventricular escape interval, an atrial escape interval, or an AV delay) is set to its IPT value and the device switches to the IPT mode at state A3. The IPT value of the escape interval used initially in the IPT mode may be a fixed value or may be based upon measurement of an intrinsic interval. While delivering IPT, the device monitors whether a specified number of senses have occurred in the cardiac chamber paced with the escape interval at state A4 and whether the period for delivering IPT has ended at state A5. If the specified number of senses (i.e., intrinsic beats) have occurred, a check is made to determine if the minimum limit value of the escape interval has been reached at state A6. If so, the IPT mode is exited at state A8. (Alternatively, the device could proceed from state A6 to state A5 and continue to deliver IPT with the present value of the escape interval.) If the minimum limit value of the escape interval has not been reached, the escape interval is shortened at state A7. The device then delivers IPT with the shortened escape interval while monitoring for senses at state A4 and for expiration of the IPT mode period at state A5. Upon expiration of the IPT mode period, the IPT mode is exited at state A8 and the device returns to state A1.

Intermittent Pacing Therapy Mode Switching

As noted above, IPT may be delivered to the ventricles in either a non-atrial tracking mode such as VVI or VOO or may be delivered in an atrial tracking mode such as DDD or VDD. A non-atrial tracking mode for IPT may be desirable in some situations because the lack of atrio-ventricular synchrony brought about by such a pacing mode may constitute an additional source of beneficial stress. For example, the device may be configured to measure the patient's intrinsic heart rate (i.e., normal sinus rhythm or NSR) while operating in the normal mode and, upon switching to the non-atrial tracking IPT mode, the LRL of the ventricular pacing mode is set to some number above the NSR (e.g., a programmable number of bpm or percentage of the NSR). The ventricles are then paced at the elevated rate during the IPT mode.

Even if it is considered preferable to use non-atrial tracking ventricular pacing at an elevated rate for the IPT mode, however, there are situations in which the IPT mode should be switched to an atrial tracking pacing mode instead. These situations could include an elevated NSR, an elevated exertion level as measured by an exertion level sensor (e.g., an accelerometer or ventilation sensor), increased heart rate variability, or the presence of an arrhythmia or pre-arrhythmic condition. The device may therefore be programmed to substitute an atrial tracking IPT mode for the non-atrial tracking IPT mode, either initially or after first starting the IPT mode with non-atrial tracking pacing, upon detection of any these conditions.

Figure 5:
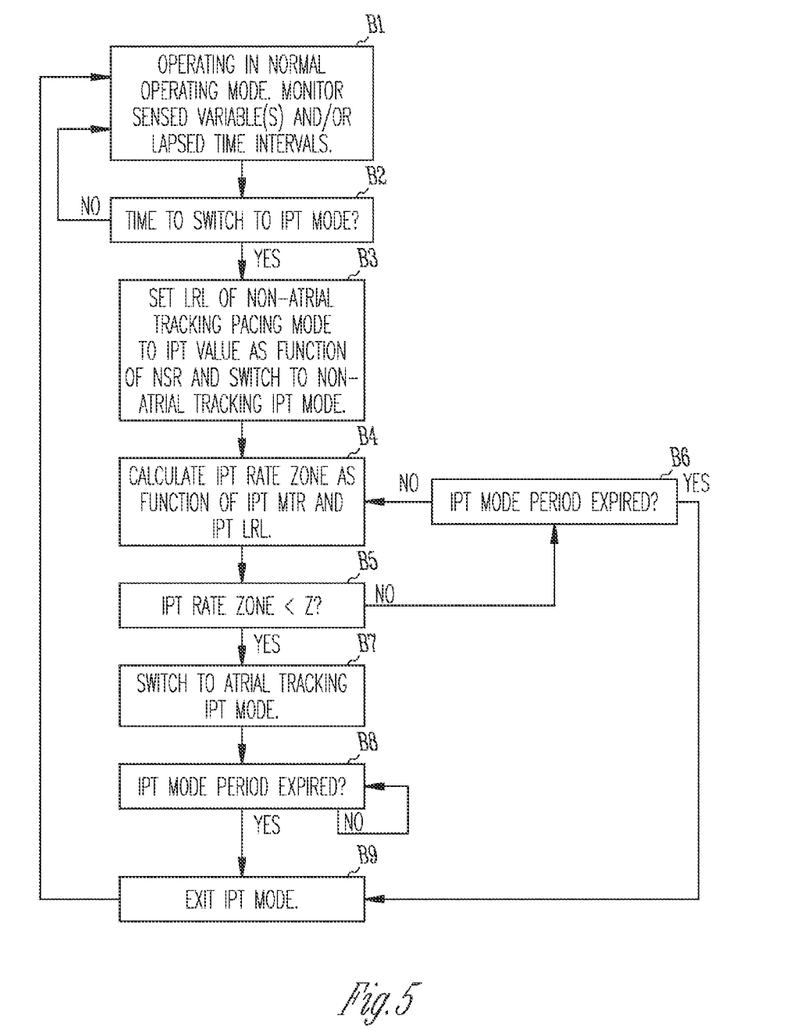
FIG. 5 illustrates an exemplary algorithm for implementing IPT mode switching.

FIG. 5 illustrates an exemplary algorithm that could be executed by the device controller that implements the IPT mode switching described above. At state B1, the device operates in a normal operating mode while monitoring lapsed time intervals and/or one or more sensed variables and checks at state B2 if it is time to switch to the IPT mode, where it is desired to use non-atrial tracking ventricular pacing for the IPT. When it is determined that a switch to the IPT mode is to made, the LRL (i.e., the inverse of the ventricular escape interval) for the IPT mode is set to some value above a measured baseline NSR of the patient, and the device switches to a non-atrial tracking IPT mode at state B3. A functional relationship between the IPT LRL and the NSR may be defined as a correspondence between different values of the variables (e.g., as implemented by a look-up table) or as an explicit calculation such as an additive constant or a specified percentage. For example, a non-atrial tracking IPT mode may be used with VVI or VOO pacing and with an IPT LRL calculated as follows:

IPT LRL=Baseline NSR+$x$ bpm(e.g., $x$=10 bpm)

The device may further calculate a rate zone for IPT that is dependent upon the programmable maximum tracking rate (MTR) of the device that is used to limit the atrial tracking rate for all pacing whether in the normal mode or an IPT mode (referred to as a global MTR). A separate maximum tracking rate for the IPT mode (referred to as an IPT MTR) is calculated as a value less than the global MTR by a specified amount. For example, the IPT MTR may be calculated as:

IPT MTR=Perm MTR-$y$ bpm (e.g., $y$=30 bpm)

A rate zone for IPT may then the calculated as:

IPT Rate Zone=IPT MTR-IPT LRL

The device may then be programmed such that if the IPT Rate Zone is less than z bpm, where z is a specified value), an atrial tracking IPT mode (e.g., VDD or DDD with a short AV delay) will be used instead. The substitution of atrial tracking pacing for non-atrial tracking pacing in the IPT mode may be made before initiation of the IPT mode after the patient's NSR is measured or may be made during the IPT mode when the non-atrial tracking pacing is delivered at a variable rate dependent upon the patient's changing NSR such the reverse hysteresis technique described above. Accordingly, at state B4, the IPT Rate Zone is calculated as a function of the IPT MTR and the IPT LRL. At state B5, the device determines if the IPT Rate Zone is less than a specified limit value z. As long as the IPT Rate Zone is not less than z, the device loops between states B4 and B5 (as the IPT LRL changes in response to, e.g., a reverse hysteresis algorithm) while testing if the IPT mode period has expired at state B6 and, if so, exiting the IPT mode at state B9. If the IPT Rate Zone is less than z, the device switches to an atrial tracking IPT mode at state B7 and continues in that mode until IPT mode expiration as determined at state B8.

Exemplary Embodiments

As described herein, a cardiac device for delivering intermittent pacing therapy (IPT) may include one or more sensing channels for sensing electrical cardiac activity, one or more pacing channels for delivering pacing pulses to one or more myocardial sites, a controller programmed to operate the device in either a normal operating mode or an IPT mode where, in the IPT mode, the controller is programmed to deliver paces to the one or more myocardial sites using a pacing mode that results in some degree of dyssynchrony as compared with the normal operating mode. The controller is programmed to intermittently switch to the IPT mode in accordance with lapsed time intervals and/or one or more sensed conditions.

In one embodiment, upon switching to the IPT mode, the controller adjusts the value of an escape interval used to deliver pacing pulses to the one or more myocardial sites to an IPT value. When operating in the IPT mode, the controller is further programmed to monitor for senses that inhibit pacing pulses to the one or more myocardial sites and shorten the escape interval used to deliver pacing pulses to the one or more myocardial sites if a specified number of such senses have occurred. The controller may be programmed to exit the IPT mode if the escape interval has been shortened to a specified minimum limit value (or a programmable number of escape events occur within a specified period of time causing the IPT session to exit) or to continue operating in the IPT mode without shortening the escape interval if the escape interval has been shortened to a specified minimum limit value. The escape interval may be a ventricular escape interval, an atrial escape interval, an AV delay used in an atrial tracking pacing mode, or an intra-ventricular delay used in biventricular pacing (e.g., RV-LV timing). The controller may be programmed to set the value of the escape interval to a programmed IPT value or may be programmed to measure one or more intrinsic cardiac intervals and set the value of the escape interval to an IPT value as a function of the intrinsic cardiac interval measurement. The controller may be programmed to shorten the escape interval by a programmed amount of time or programmed to shorten the escape interval by a programmed percentage of the value of the escape interval currently being used.

In another embodiment, the controller is programmed to deliver paces to the one or more ventricular sites in the IPT mode using an atrial tracking or a non-atrial tracking pacing mode that results in some degree of ventricular dyssynchrony as compared with the normal operating mode and to intermittently switch to the IPT mode in accordance with a predetermined duty cycle. The controller is further programmed to measure a present intrinsic heart rate or normal sinus rhythm (NSR) and to initially use a non-atrial tracking ventricular pacing mode with an IPT LRL set above the NSR for the IPT mode unless the NSR is above a specified limit value, in which case an atrial tracking ventricular pacing mode is used for the IPT mode. The controller may also be programmed to employ reverse hysteresis in the non-atrial tracking IPT mode and switch to an atrial tracking IPT mode if the pacing rate rises to a specified extent. That is, when operating in the IPT mode using non-atrial tracking pacing, the controller monitors for senses that inhibit pacing pulses to the one or more myocardial sites and increases the IPT LRL used to deliver pacing pulses to the one or more ventricular sites if a specified number of such senses have occurred. The controller then switches to an atrial tracking pacing mode for the IPT mode if the LRL is above a specified limit value.

The invention has been described in conjunction with the foregoing specific embodiments. It should be appreciated that those embodiments may also be combined in any manner considered to be advantageous. Also, many alternatives, variations, and modifications will be apparent to those of ordinary skill in the art. Other such alternatives, variations, and modifications are intended to fall within the scope of the following appended claims.

What is claimed is:

1. A cardiac device, comprising:
one or more sensing amplifiers for sensing electrical cardiac activity through one or more sensing channels;
one or more pulse generators for delivering pacing pulses to one or more myocardial sites through one or more pacing channels;
an exertion level sensor for measuring exertion level;
a controller programmed to operate the device in either a normal operating mode or an intermittent pacing therapy (IPT) mode;
wherein, in the IPT mode, the controller is programmed to deliver paces to the one or more myocardial sites using a pacing mode that results in some degree of dyssynchrony as compared with the normal operating mode;
wherein the controller is programmed to intermittently switch to the IPT mode that delivers ventricular pacing pulses with an escape interval initially set to a specified IPT value;
wherein the controller is programmed to switch to a non-atrial tracking IPT mode if the measured exertion level is below a specified value and switch to an atrial tracking IPT mode otherwise;
wherein, when operating in the IPT mode, the controller is further programmed to monitor for senses that inhibit the ventricular pacing pulses and, after a specified number of such senses have occurred, further shorten the escape interval from the IPT value; and,
wherein the controller is further programmed to continue operating in the IPT mode without shortening the escape interval if the escape interval has been shortened to a specified minimum limit value.

2. The device of claim 1 wherein the controller is further programmed to exit the IPT mode if the escape interval has been shortened to a specified minimum limit value.

3. The device of claim 1 wherein the atrial tracking IPT mode is VDD.

4. The device of claim 1 wherein the atrial tracking IPT mode is DDD.

5. The device of claim 1 wherein the exertion level sensor is a minute ventilation sensor.

6. The device of claim 1 wherein the exertion level sensor is an accelerometer.

7. The device of claim 1 wherein the controller is programmed to measure one or more intrinsic cardiac intervals and set the value of the escape interval to an IPT value as a function of the intrinsic cardiac interval measurement.

8. The device of claim 1 wherein the controller is programmed to shorten the escape interval by a programmed amount of time.

9. The device of claim 1 wherein the controller is programmed to shorten the escape interval by a programmed percentage of the value of the escape interval currently being used.

10. The device of claim 1 wherein the IPT mode is initially a non-atrial tracking ventricular pacing mode and wherein the controller is programmed to switch to an atrial tracking IPT mode if the escape interval is shortened below a specified limit value.

11. A method for operating a cardiac device, comprising:
sensing electrical cardiac activity through one or more sensing channels;
delivering pacing pulses to one or more myocardial sites through one or more pacing channels;
measuring exertion level;
operating the device in either a normal operating mode or an intermittent pacing therapy (IPT) mode;
wherein, in the IPT mode, the paces are delivered to the one or more myocardial sites using a pacing mode that results in some degree of dyssynchrony as compared with the normal operating mode;
in the IPT mode, delivering ventricular pacing pulses with an escape interval initially set to a specified IPT value;
intermittently switching to the IPT mode;
switching to a non-atrial tracking IPT mode if the measured exertion level below a specified value and switching to an atrial tracking IPT mode otherwise;
when operating in the IPT mode, monitoring for senses that inhibit the ventricular pacing pulses and, after a specified number of such senses have occurred, further shortening the escape interval from the IPT value; and,
continuing operating in the IPT mode without shortening the escape interval if the escape interval has been shortened to a specified minimum limit value.

12. The method of claim 11 further comprising exiting the IPT mode if the escape interval has been shortened to a specified minimum limit value.

13. The method of claim 11 wherein the atrial tracking IPT mode is VDD.

14. The method of claim 11 wherein the atrial tracking IPT mode is DDD.

15. The method of claim 11 wherein the exertion level is measured with a minute ventilation sensor.

16. The method of claim 11 wherein the exertion level is measured with an accelerometer.

17. The method of claim 11 further comprising measuring one or more intrinsic cardiac intervals and setting the value of the escape interval to an IPT value as a function of the intrinsic cardiac interval measurement.

18. The method of claim 11 wherein the IPT mode is initially a non-atrial tracking ventricular pacing mode and further comprising switching to an atrial tracking IPT mode if the escape interval is shortened below a specified limit value.

* * * * *